US00PP31912P2

(12) United States Plant Patent
Bourne

(10) Patent No.: US PP31,912 P2
(45) Date of Patent: Jun. 30, 2020

(54) GRAPEVINE NAMED 'SV27-104-114'

(50) Latin Name: *Vitis vinifera*
Varietal Denomination: SV27-104-114

(71) Applicant: Sunview Vineyards of California, Inc, Delano, CA (US)

(72) Inventor: Timothy F. Bourne, Visalia, CA (US)

( * ) Notice: Subject to any disclaimer, the term of this patent is extended or adjusted under 35 U.S.C. 154(b) by 0 days.

(21) Appl. No.: 16/350,599

(22) Filed: Dec. 6, 2018

Related U.S. Application Data

(60) Provisional application No. 62/708,990, filed on Dec. 28, 2017.

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 6/88
See application file for complete search history.

*Primary Examiner* — Annette H Para
(74) *Attorney, Agent, or Firm* — Baker Manock & Jensen, PC; Eric C. Cole

(57) ABSTRACT

A new and distinct variety of grapevine named 'SV27-104-114' particularly characterized by its unusual, cylindrical shaped berries, medium firm texture, and very large, sweet berries. Additionally, berries of the new cultivar are very responsive to applications of exogenous gibberellic acid and trunk girdling, almost doubling in size in comparison to untreated fruit.

2 Drawing Sheets

Latin name of the genus and species of the plant claimed: The plant claimed relates to a new and distinct variety of *Vitis vinifera*.

Variety denomination: The plant claimed shall be known as 'SV27-104-114'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV27-104-114'. As used herein, 'grapevine' refers to all plant parts including, vines, canes, tendrils, leaves, fruit and roots of grapevine named 'SV27-104-114'. Grapevine named 'SV27-104-114' is the result of an effort to produce a late season red, seedless cultivar superior to 'Crimson Seedless' (unpatented). This new cultivar originated from a cross conducted in May 2006 near McFarland, Calif. between grapevine plant selection 'SV18-6-568' (unpatented) and grapevine plant 'SV22-89e-543' (unpatented). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in November of 2006 and grown in the greenhouse at 29° C. with 12 hours illumination under high pressure sodium vapor lamps. The seedling population of 72 plants was planted in the field in the spring of 2007 near McFarland, Calif. The new grapevine was selected from this seedling population on Sep. 7, 2010. It was then propagated by cuttings and grafted to 'Freedom' (unpatented) rootstock in 2011. The present invention has been found to retain its distinctive characteristics through two successive asexual propagations.

Grapevine named 'SV27-104-114' differs from its female parent grapevine 'SV18-6-568' (unpatented) in that 'SV27-104-114' has cylindrical shaped, seedless berries, whereas 'SV18-6-568' has ellipsoidal shaped berries.

Grapevine named 'SV27-104-114' differs from its male parent, 'SV22-89e-543' (unpatented) in that grapevine named 'SV27-104-114' has bright red berries whereas 'SV22-89e-543' has green to white berries.

Grapevine named 'SV27-104-114' differs from the commercial cultivar 'Crimson Seedless' in that grapevine named 'SV27-104-114' has cylindrical shaped, bright red berries, whereas 'Crimson Seedless' has ellipsoidal shaped, red berries. The berries of grapevine named 'SV27-104-114' are larger at harvest after standard vineyard practices of application of exogenous gibberellic acid and girdling of the vine trunks as compared to 'Crimson Seedless'. Additionally, grapevine named 'SV27-104-114' has fruitful shoots with spur pruning to two buds, whereas 'Crimson Seedless' lacks fruitfulness with spur pruning only. The texture of grapevine named 'SV27-104-114' is generally softer than that of 'Crimson Seedless'.

Grapevine named 'SV27-104-114' is most similar to commercial cultivar 'Scarlet Royal' (U.S. Plant Pat. No. 16,229). The natural berry size of grapevine named 'SV27-104-114' is smaller than that of 'Scarlet Royal' (U.S. Plant Pat. No. 16,229) but approximately equals that of 'Scarlet Royal' (U.S. Plant Pat. No. 16,229) with application of exogenous gibberellic acid and trunk girdling. It may be distinguished from 'Scarlet Royal' (U.S. Plant Pat. No.

16,229) by its brighter red coloration of berries and lower plant vigor. Additionally, grapevine named 'SV27-104-114' does not develop astringent flavors in its fruit at full ripeness as does 'Scarlet Royal' (U.S. Plant Pat. No. 16,229).

SUMMARY OF THE INVENTION

The following are the most outstanding and distinguishing characteristics of this new variety when grown under normal horticultural practices near McFarland, Calif.:

1. Berries are bright red in color;
2. Berry texture is slightly soft to moderately firm at harvest; and
3. Berry shape is elongate, cylindrical in shape with sweet taste.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from a plant about 6 years-old, grown in a field near McFarland, Calif. in 2016.

DETAILED BOTANICAL DESCRIPTION

Figure 1:
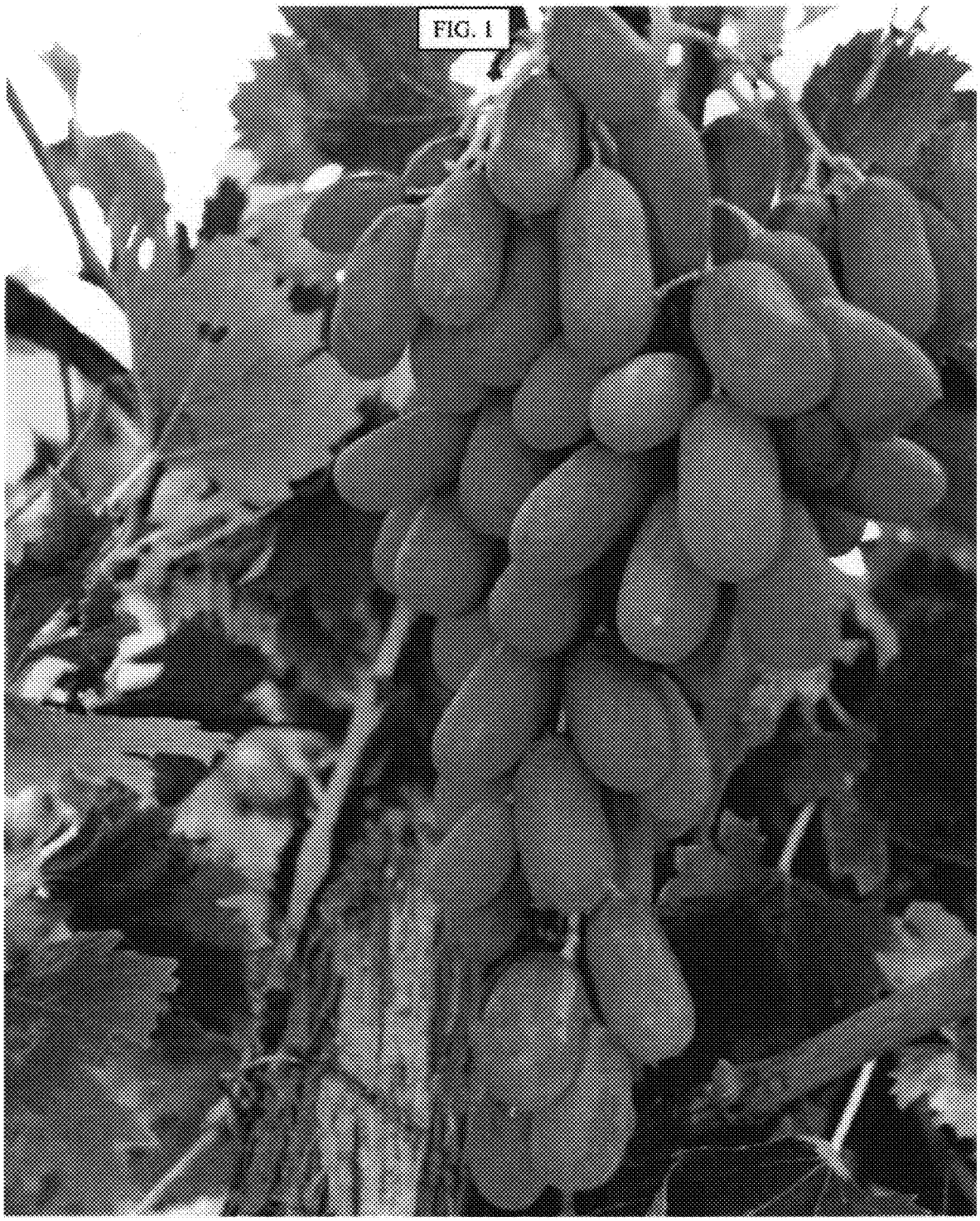
FIG. 1 Fruit cluster on the vine.
Figure 2:
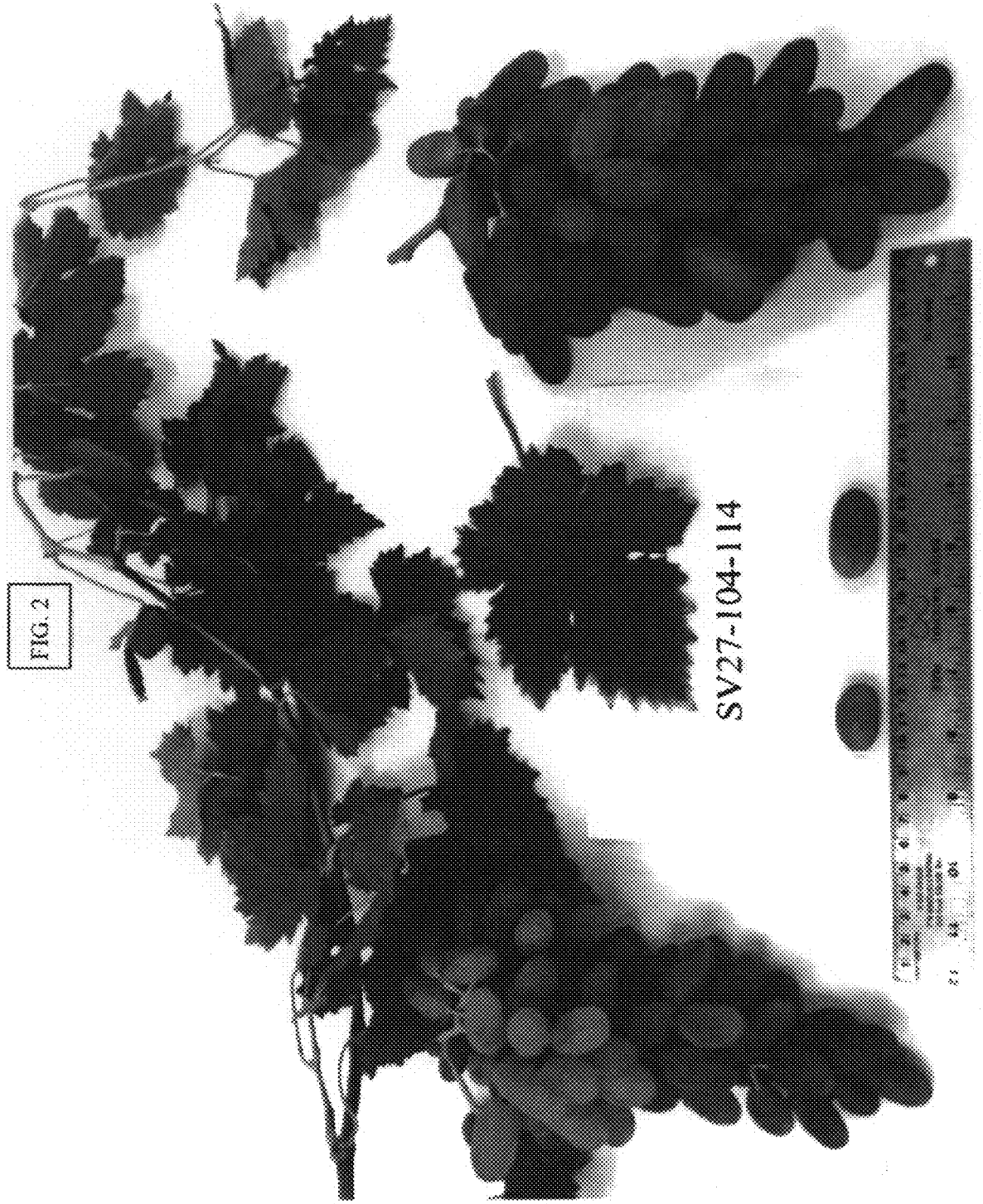
FIG. 2 Fruit and leaves from naturally growing vines and cluster of fruit from a vine to which exogenous gibberellic acid was applied along with trunk girdling.

The following detailed description sets forth the distinctive characteristics of grapevine named 'SV27-104-114'. Descriptions of the new invention apply to vines of grapevine named 'SV27-104-114' grown on 'Freedom' rootstock at a density of 1,281 vines per hectare grown near McFarland, Calif. in 2017. These vines were in their sixth year of full production having been planted in 2011. These descriptions are believed to apply generally to the new variety grown under similar circumstances elsewhere. Color references are primarily to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV27-104-114'.

Plant:

*Vigor*.—Medium; vines spur-pruned and shoot thinned to 32 shoots.
*Density of foliage*.—Moderate.
*Productivity*.—Moderately productive when spur pruned, up to 16,593 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.
*Color outer bark*.—RHS 201A (grey group).
*Color inner bark*.—RHS 166C (greyed orange group).
*Trunk circumference, eight year old vine at 1 meter height*.—23 cm.

Mature leaves:

*Average blade length*.—9.5 cm.
*Average blade width*.—11.7 cm.
*Size of blade*.—Medium.
*Shape*.—Pentagonal.
*Number of lobes*.—5.
*Mature leaf profile*.—Cupped upwards on lower lobes of leaves.
*Blistering* (*upper surface*).—Absent.
*Leaf blade tip*.—In plane of leaf.
*Margins*.—Lobed, serrated, undulating, lower lobes cupped upward.
*Apex*.—Broadly acuminate.
*Bases*.—Sagittate.
*Thickness*.—Medium.
*Undulation of blade between main and lateral veins*.—Slight.
*Shape of teeth*.—Broadly conical, both sides convex.
*Length of teeth*.—3.0 to 10.0 mm.
*Ratio length/width of teeth*.—About 1:1.
*General shape of petiole sinus*.—Wide open.
*Tooth at petiole sinus*.—Absent.
*Petiole sinus limited by veins*.—Absent.
*Shape of upper lateral sinus*.—Open to fully closed.
*Upper surface*.—Summer color: RHS 137B (green group). Anthocyanin coloration of main veins on the upper side of the blade: Present only at base of main veins. Prostrate hairs on main veins (upper surface): Absent. Surface texture: Smooth. Surface appearance: Dull. Goffering of blade: Absent.
*Lower surface*.—Summer color: RHS 137C (green group). Anthocyanin coloration of main veins on lower leaf surface: Limited to bases of main veins near petiole junction. Anthocyanin coloration on laterals: None. Prostrate hairs between veins (lower surface): Absent. Erect hairs between veins (lower surface): Absent. Prostrate hairs on main veins (lower surface): Sparse, limited to junction of main veins to petiole. Density of erect hairs on main veins (lower surface): Sparse; found only at the base of the main veins. Glossiness: Low. Pubescence: Absent. Surface texture: Rough. Surface appearance: Dull.
*Petiole*.—Length: 5.8 cm. Diameter: About 2 mm. Length of petiole compared to middle vein: Much shorter. Density of prostrate hairs: Absent. Density of erect hairs: Absent. Shape of base of petiole sinus: Mostly open; outline is conical. Color: In sun: RHS 185A (greyed purple group).

Tendrils:

*Number*.—Bifurcated and trifurcated; forming at and above node 7.
*Length*.—18.0 cm to 22.5 cm.
*Diameter*.—About 1.5 mm.
*Texture*.—Smooth.
*Color*.—RHS N144A (yellow green group).

Growing tips (young shoot):

*Pubescence*.—Abundant, prostate.
*Color*.—RHS 144B (yellow green group).
*Anthocyanins*.—Absent.
*Shape*.—Rounded.

*Apex*.—Fully open.

*Shoot attitude*.—Semi-erect.

Young shoots:

*Color young shoot upper surface exposed to light*.—RHS 184A (greyed purple group).

*Color young shoot lower surface*.—RHS 144A (yellow green group).

*Color internodes upper surface*.—RHS 145B (yellow green group).

*Color internodes lower surface*.—RHS 144B (yellow green group).

*Color nodes, upper surface*.—RHS 144B (yellow green group).

*Color nodes, lower surface*.—RHS 144C (yellow green group).

*Erect hairs internodes*.—Absent.

Mature Canes:

*Color mature cane internode upper surface*.—RHS 166C (greyed orange group).

*Color mature cane internode lower surface*.—RHS 167C (greyed orange group).

*Color mature cane node upper surface*.—RHS 166A (greyed orange group).

*Color mature cane node lower surface*.—RHS 166A (greyed orange group).

*Mature cane annual growth*.—239 cm.

Fruit:

*Ripening period*.—Mid-season, about 10 days after 'Princess' at McFarland, Calif.

*Date of ripening*.—August 22 at McFarland, Calif.

*Use*.—Fresh market.

*Keeping quality*.—Very good.

*Shipping quality*.—Very good.

*Date of first harvest*.—August 22.

*Solids-sugar*.—High, about 22 brix at full maturity.

*Bunch*.—Size: Medium. Length (peduncle excluded): About 20 to 30 cm. Width: About 13 cm. Weight: Natural, without gibberellic acid treatment: 615.0 g. With gibberellic acid treatment and trunk girdling: 670.0 g. Density: Well-filled, but loose. Number of berries: 85. Form: Conical.

*Peduncle*.—Length: About 3.5 cm. Lignification: Medium. Color: RHS 143B (green group).

*Berry*.—Size: Large. Uniformity of size: Uniform. Weight. Natural, without gibberellic acid treatment: About 5 g. With gibberellic acid treatment: About 8 g. Shape: Natural, without gibberellic acid treatment: Cylindrical. With gibberellic acid treatment: Cylindrical. Presence of seeds: Seedless; most berries develop one or two small, partially lignified, rudimentary seeds about 5-6 mm in length. Cross section: Circular. Dimensions: Natural berry, longitudinal axis: About 3.0 cm. Natural berry horizontal axis: About 1.6 cm. Gibbed and girdled, longitudinal axis: About 3.8 cm. Gibbed and girdled, horizontal axis: About 1.9 cm. Skin color (without bloom): RHS 45C (red group). Coloration of flesh: Translucent; RHS 150D (yellow green group). Juiciness of flesh: Very juicy. Berry firmness: Soft to moderately firm. Particular flavor: Neutral, typical *vinifera*. Bloom (cuticular wax): Strong. Pedicel length: 1.0 cm. Berry separation from pedicel: With difficulty.

*Skin*.—Thickness: Medium. Texture: Tender. Reticulation: Absent. Roughness: Slight. Tenacity: Tenacious to flesh. Tendency to crack: Resistant.

Disease and insect resistance: No particular resistance or susceptibility has been observed. Normal disease control practices can be used.

Having thus described and illustrated our new variety of grapevine, we claim:

1. A new and distinct variety of grapevine named 'SV27-104-114', and parts thereof, substantially as illustrated and described herein.

* * * * *